(12) United States Patent
Oglaza et al.

(10) Patent No.: US 9,579,130 B2
(45) Date of Patent: Feb. 28, 2017

(54) APPARATUS FOR RESTORATION OF THE SPINE AND METHODS OF USE THEREOF

(75) Inventors: Jean-François Oglaza, Balma (FR); Cécile Vienney, Lugos (FR)

(73) Assignee: Vexim SAS, Balma (FR)

(*) Notice: Subject to any disclaimer, the term of this patent is extended or adjusted under 35 U.S.C. 154(b) by 413 days.

(21) Appl. No.: 12/417,565

(22) Filed: Apr. 2, 2009

(65) Prior Publication Data

US 2009/0281628 A1 Nov. 12, 2009

Related U.S. Application Data

(63) Continuation of application No. PCT/IB2008/002246, filed on Apr. 8, 2008.

(51) Int. Cl.
*A61B 17/70* (2006.01)
*A61F 2/44* (2006.01)
*A61F 2/30* (2006.01)

(52) U.S. Cl.
CPC ............ *A61B 17/7065* (2013.01); *A61F 2/446* (2013.01); *A61F 2002/3055* (2013.01);
(Continued)

(58) Field of Classification Search
CPC ............. A61B 17/7065; A61B 17/7062; A61F 2002/30471; A61F 2002/30579; A61F 2002/30411; A61F 2002/30462; A61F 2220/0091
USPC ........... 606/68, 90, 105, 246–249, 313, 320, 606/326–327, 79; 623/17.11, 17.13, 623/17.15, 17.12, 17.14, 17.16
See application file for complete search history.

(56) References Cited

U.S. PATENT DOCUMENTS

| 4,796,612 A | 1/1989 | Reese |
| 4,932,975 A | 6/1990 | Main et al. |

(Continued)

FOREIGN PATENT DOCUMENTS

| CN | 1162349 A | 10/1997 |
| CN | 1713863 A | 12/2005 |

(Continued)

OTHER PUBLICATIONS

International Search Report and Written Opinion of the International Searching Authority corresponding to International PCT/IB2005/002631 date of mailing Feb. 7, 2006.

(Continued)

*Primary Examiner* — Jan Christopher Merene
*Assistant Examiner* — Atiya Mahmud
(74) *Attorney, Agent, or Firm* — Cooley LLP

(57) ABSTRACT

The subject disclosure are directed to systems, apparatuses, devices and methods for vertebral and spinal correction. In some embodiments, an expansible implant is provided which may be inserted between two vertebrae, for instance, for maintenance and/or restoration of the distance/space between vertebrae. The implant may include first and second opposed plates that are intended to move away from one another, and which engage portions of vertebrae via a recess provided for on a bearing surface of the plates. The implant may additionally include at least first and second opposed end members, where at least one of the end members includes an aperture configured for receiving at least a portion of a retaining element adapted for retaining the implant in an expanded configuration once the implant is expanded. Methods of treatment and methods of use of such implants for the alleviation of back pain (for example) are also provided herein.

24 Claims, 9 Drawing Sheets

(52) U.S. Cl.
CPC ............... *A61F 2002/30411* (2013.01); *A61F 2002/30462* (2013.01); *A61F 2002/30471* (2013.01); *A61F 2002/30579* (2013.01); *A61F 2002/30583* (2013.01); *A61F 2002/30594* (2013.01); *A61F 2210/0085* (2013.01); *A61F 2220/0025* (2013.01); *A61F 2220/0075* (2013.01); *A61F 2220/0091* (2013.01); *A61F 2310/00023* (2013.01)

(56) References Cited

U.S. PATENT DOCUMENTS

| | | | |
|---|---|---|---|
| 4,961,740 A | 10/1990 | Ray et al. | |
| 4,969,888 A | 11/1990 | Scholten et al. | |
| 5,059,193 A | 10/1991 | Kuslich | |
| 5,108,404 A | 4/1992 | Scholten et al. | |
| 5,665,122 A | 9/1997 | Kambin et al. | |
| 5,693,100 A * | 12/1997 | Pisharodi | 623/17.16 |
| 5,695,515 A | 12/1997 | Orejola | |
| 5,720,746 A | 2/1998 | Soubeiran | |
| 5,800,550 A | 9/1998 | Sertich | |
| 5,908,448 A | 6/1999 | Roberts et al. | |
| 5,972,015 A | 10/1999 | Scribner et al. | |
| 5,980,522 A | 11/1999 | Koros et al. | |
| 6,039,761 A | 3/2000 | Li et al. | |
| 6,066,154 A | 5/2000 | Reiley et al. | |
| 6,102,950 A * | 8/2000 | Vaccaro | 623/17.16 |
| 6,126,689 A | 10/2000 | Brett | |
| 6,127,597 A | 10/2000 | Beyar et al. | |
| 6,176,882 B1 * | 1/2001 | Biedermann et al. | 623/17.15 |
| 6,190,414 B1 | 2/2001 | Young et al. | |
| 6,193,757 B1 | 2/2001 | Foley et al. | |
| 6,197,033 B1 | 3/2001 | Haid, Jr. et al. | |
| 6,214,050 B1 | 4/2001 | Huene | |
| 6,235,043 B1 | 5/2001 | Reiley et al. | |
| 6,248,110 B1 | 6/2001 | Reiley et al. | |
| 6,261,289 B1 | 7/2001 | Levy | |
| 6,280,456 B1 | 8/2001 | Scribner et al. | |
| 6,332,895 B1 | 12/2001 | Suddaby | |
| 6,395,031 B1 | 5/2002 | Foley et al. | |
| 6,423,083 B2 | 7/2002 | Reiley et al. | |
| 6,454,807 B1 | 9/2002 | Jackson | |
| 6,488,710 B2 | 12/2002 | Besselink | |
| 6,554,833 B2 | 4/2003 | Levy et al. | |
| 6,582,431 B1 | 6/2003 | Ray | |
| 6,595,998 B2 | 7/2003 | Johnson et al. | |
| 6,607,544 B1 | 8/2003 | Boucher et al. | |
| 6,623,505 B2 | 9/2003 | Scribner et al. | |
| 6,632,235 B2 | 10/2003 | Weikel et al. | |
| 6,663,647 B2 | 12/2003 | Reiley et al. | |
| 6,664,897 B2 | 12/2003 | Pape et al. | |
| 6,676,665 B2 | 1/2004 | Foley et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,740,093 B2 | 5/2004 | Hochschuler et al. | |
| 6,783,530 B1 | 8/2004 | Levy | |
| 6,929,647 B2 | 8/2005 | Cohen | |
| 6,953,477 B2 * | 10/2005 | Berry | 623/17.11 |
| 6,979,341 B2 | 12/2005 | Scribner et al. | |
| 6,981,981 B2 | 1/2006 | Reiley et al. | |
| 7,044,954 B2 | 5/2006 | Reiley et al. | |
| 7,070,598 B2 | 7/2006 | Lim et al. | |
| 7,087,055 B2 | 8/2006 | Lim et al. | |
| 7,153,306 B2 | 12/2006 | Ralph et al. | |
| 7,217,293 B2 | 5/2007 | Branch, Jr. | |
| 7,234,468 B2 | 6/2007 | Johnson et al. | |
| 7,241,303 B2 | 7/2007 | Reiss et al. | |
| 7,261,720 B2 | 8/2007 | Stevens et al. | |
| 7,264,622 B2 | 9/2007 | Michelson | |
| 7,318,839 B2 | 1/2008 | Malberg et al. | |
| 7,621,950 B1 | 11/2009 | Globerman et al. | |
| 7,763,028 B2 * | 7/2010 | Lim et al. | 606/90 |
| 7,799,080 B2 * | 9/2010 | Doty | 623/17.15 |
| 7,879,104 B2 * | 2/2011 | Dewey et al. | 623/17.16 |
| 8,328,818 B1 | 12/2012 | Seifert et al. | |
| 2001/0032020 A1 | 10/2001 | Besselink | |
| 2002/0065548 A1 | 5/2002 | Birdsall et al. | |
| 2002/0120327 A1 | 8/2002 | Cox et al. | |
| 2002/0151976 A1 | 10/2002 | Foley et al. | |
| 2002/0198532 A1 | 12/2002 | Michelson | |
| 2003/0065396 A1 * | 4/2003 | Michelson | 623/17.15 |
| 2003/0074064 A1 | 4/2003 | Gerbec et al. | |
| 2003/0171812 A1 | 9/2003 | Grunberg et al. | |
| 2003/0220650 A1 | 11/2003 | Major et al. | |
| 2003/0236520 A1 | 12/2003 | Lim et al. | |
| 2004/0073308 A1 | 4/2004 | Kuslich et al. | |
| 2004/0087947 A1 | 5/2004 | Lim et al. | |
| 2004/0102774 A1 | 5/2004 | Trieu | |
| 2004/0167625 A1 | 8/2004 | Beyar et al. | |
| 2004/0210231 A1 | 10/2004 | Boucher et al. | |
| 2004/0215343 A1 | 10/2004 | Hochschuler et al. | |
| 2005/0107800 A1 | 5/2005 | Frankel et al. | |
| 2005/0143827 A1 | 6/2005 | Globerman et al. | |
| 2005/0182416 A1 | 8/2005 | Lim et al. | |
| 2005/0222681 A1 * | 10/2005 | Richley et al. | 623/17.11 |
| 2005/0228391 A1 | 10/2005 | Levy et al. | |
| 2005/0273135 A1 * | 12/2005 | Chanduszko et al. | 606/213 |
| 2006/0004455 A1 * | 1/2006 | Leonard et al. | 623/17.15 |
| 2006/0085070 A1 | 4/2006 | Kim | |
| 2006/0149379 A1 * | 7/2006 | Kuslich et al. | 623/17.12 |
| 2006/0271049 A1 | 11/2006 | Zucherman et al. | 606/61 |
| 2007/0016303 A1 * | 1/2007 | Jackson | 623/17.16 |
| 2007/0021836 A1 * | 1/2007 | Doty | 623/17.13 |
| 2007/0032790 A1 * | 2/2007 | Aschmann et al. | 606/61 |
| 2007/0032791 A1 | 2/2007 | Greenhalgh | |
| 2007/0142915 A1 * | 6/2007 | Altarac et al. | 623/17.11 |
| 2007/0173826 A1 * | 7/2007 | Canaveral et al. | 606/61 |
| 2007/0173832 A1 * | 7/2007 | Tebbe et al. | 606/61 |
| 2007/0260315 A1 * | 11/2007 | Foley et al. | 623/17.12 |
| 2008/0051894 A1 * | 2/2008 | Malandain et al. | 623/17.11 |
| 2008/0065087 A1 | 3/2008 | Osorio et al. | |
| 2008/0065089 A1 | 3/2008 | Osorio et al. | |
| 2008/0086133 A1 | 4/2008 | Kuslich et al. | |
| 2008/0114367 A1 * | 5/2008 | Meyer | 606/90 |
| 2008/0125784 A1 | 5/2008 | Rabiner et al. | |
| 2008/0140079 A1 | 6/2008 | Osorio et al. | |
| 2008/0140207 A1 * | 6/2008 | Olmos et al. | 623/17.16 |
| 2008/0147193 A1 * | 6/2008 | Matthis et al. | 623/17.16 |
| 2008/0167657 A1 * | 7/2008 | Greenhalgh | 606/90 |
| 2009/0171390 A1 * | 7/2009 | Sankaran | 606/246 |
| 2009/0228012 A1 | 9/2009 | Gangji et al. | |
| 2009/0306715 A1 * | 12/2009 | Jackson et al. | 606/249 |
| 2009/0326581 A1 * | 12/2009 | Galley et al. | 606/249 |

FOREIGN PATENT DOCUMENTS

| | | |
|---|---|---|
| CN | 101031259 A | 9/2007 |
| EP | 0796593 A2 | 9/1997 |
| FR | 2782632 A1 | 3/2000 |
| GB | 2 435 292 A | 9/2007 |
| JP | 2006507090 A | 3/2006 |
| JP | 2008501462 A | 1/2008 |
| WO | 98/34568 A1 | 8/1998 |
| WO | 99/52447 A1 | 10/1999 |
| WO | WO 01/01895 A1 | 1/2001 |
| WO | 01/60263 A1 | 8/2001 |
| WO | WO 01/54598 A1 | 8/2001 |
| WO | WO 01/66047 A1 | 9/2001 |
| WO | WO 03/003951 A1 | 1/2003 |
| WO | 2004/019756 A2 | 3/2004 |
| WO | WO 2004/026188 A2 | 4/2004 |
| WO | WO 2004/026188 A3 | 4/2004 |
| WO | WO 2004/034924 A2 | 4/2004 |
| WO | WO 2004/034924 A3 | 4/2004 |
| WO | WO 2004/047689 A1 | 6/2004 |
| WO | WO 2004/086934 A2 | 10/2004 |
| WO | WO 2004/086934 A3 | 10/2004 |
| WO | 2005/048856 A1 | 6/2005 |
| WO | WO 2005/120400 A1 | 12/2005 |
| WO | WO 2006/068682 A1 | 6/2006 |
| WO | WO 2006/116760 A2 | 11/2006 |
| WO | WO 2007/041665 A2 | 4/2007 |
| WO | WO 2007/041665 A3 | 4/2007 |

(56) References Cited

FOREIGN PATENT DOCUMENTS

| WO | WO 2007/073488 A2 | 6/2007 |
|----|----|----|
| WO | WO 2007/073488 A3 | 6/2007 |
| WO | WO 2007/075788 A2 | 7/2007 |
| WO | WO 2007/076308 A2 | 7/2007 |
| WO | WO 2007/076374 A2 | 7/2007 |
| WO | WO 2007/076374 A3 | 7/2007 |
| WO | WO 2007/076376 A2 | 7/2007 |
| WO | WO 2007/076376 A3 | 7/2007 |
| WO | WO 2007/079237 A2 | 7/2007 |
| WO | WO 2007/084239 | 7/2007 |
| WO | 2010/100287 A1 | 9/2010 |
| WO | 2010/103344 A1 | 9/2010 |

OTHER PUBLICATIONS

French Preliminary Search Report corresponding to French Patent Application No. 04 06211 dated Feb. 15, 2005.
French Preliminary Search Report corresponding to French Patent Application No. 05 05798 dated Oct. 28, 2005.
International Search Report corresponding to International PCT/IB2008/002246 dated Jan. 29, 2009.
International Preliminary Report on Patentability issued Sep. 13, 2011 for PCT/IB2009/005385, filed Mar. 12, 2009.
International Search Report mailed Dec. 12, 2009 and Written Opinion for PCT/IB2009/005385, filed Mar. 12, 2009.
International Preliminary Report on Patentability issued Dec. 14, 2006 for PCT/IB2005/002631, filed Jun. 8, 2005.
International Preliminary Report on Patentability issued Oct. 12, 2010 for PCT/IB2008/002246, filed Apr. 8, 2008.
International Search Report mailed Dec. 6, 2011 for PCT/IB2011/001480, filed Apr. 7, 2011.
International Preliminary Report on Patentability issued Oct. 8, 2013 for PCT/IB2011/001480, filed Apr. 7, 2011.
European Search Report mailed Feb. 22, 2013 for EP Application No. 12191848.6, filed Jun. 8, 2005.
Supplementary Search Report issued on Apr. 8, 2014, by the State Intellectual Property Office of the People's Rep. of China for Application No. 200980159243.7, filed Mar. 12, 2009.

* cited by examiner

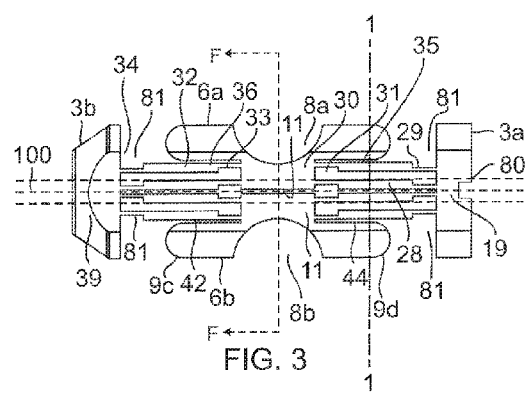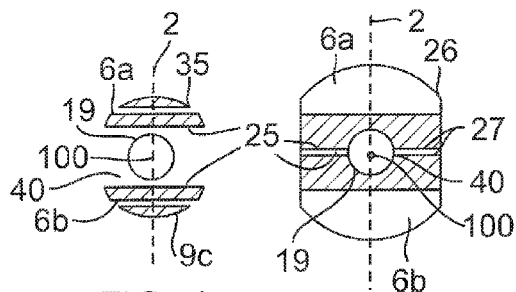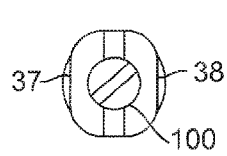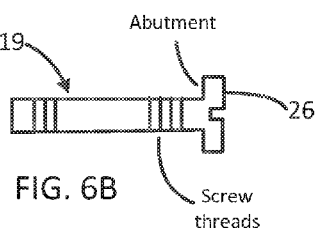

Coupe III-III

Coupe IV-IV

Coupe V-V

Coupe VI-VI

APPARATUS FOR RESTORATION OF THE SPINE AND METHODS OF USE THEREOF

RELATED APPLICATIONS

This application is a continuation of PCT Application No. PCT/IB2008/002246 filed Apr. 8, 2008 under 35 USC §111(a). Priority of the aforementioned filing date is hereby claimed, and the disclosure of the PCT Patent Application is hereby incorporated by reference in its entirety.

FIELD OF THE DISCLOSURE

Embodiments of the present disclosure are directed to spinal implants, and more particularly, to intervertebral spinous implants.

BACKGROUND OF THE DISCLOSURE

The spinal column is made up of four main components: the spinal chord, the vertebra, the ligaments, and the intervertebral disc, and each may play a role in back pain. Generally, back pain may be caused by spinal instability, disc or ligament degeneration, bone joint dislocation, spinal root or articulation compression, and the like. For instance, deterioration of the intervertebral disc, such as a result of spinal stenosis, can lead to extreme discomfort and pain.

Accordingly, a common source of back pain is the result of the degeneration or herniation of the intervertebral disc, causing compression of the spinal column, which in turn can lead to the pinching of the spinal nerves and the release of inflammatory chemical mediators that promote swelling and inflammation thereby further irritating spinal nerves.

One method used for the relief of back pain, such as that caused by spinal stenosis, involves surgery designed to remove and/or reduce pressure on the spinal nerves/roots caused by such mechanical breakdown of the spinal column. Several techniques, such as interspinous process decompression, are known for effecting a vertebral correction, e.g., to attempt to restore an intervertebral space to its original shape or distance.

For instance, where back pain is caused by deterioration of the intervertebral disc, intervertebral implants, such as cages or disc prosthesis, have been designed to be inserted into the deteriorated region between two vertebral endplates in an effort to stabilize or increase the space between the vertebrae. Such intervertebral implants, however, limit the extent to which vertebrae can move towards each other since, when the spine is extended, spinous processes tend to come into abutment against the surfaces of the implants. Furthermore, since implants do not have the same mechanical properties as that of an intervertebral disc, the overall mechanical properties of the spine present significant discontinuities compared with an intact spine, thereby increasing deterioration of the intervertebral disc.

Accordingly, there is a need in the art for a spinal implant and corresponding associated methods (e.g. method of use) that reduce the above noted disadvantages of implants that are used to address spinal complications, and provide for the reduction of back pain as well as the restoration of the spine. At least some of the embodiments of the present disclosure meet these and other needs in the art.

SUMMARY OF THE DISCLOSURE

Some of the embodiments of the subject disclosure are directed toward an expansible/expandable implant. The implant may be inserted between two portions of a vertebra, or within an intervertebral space between two vertebrae, for the restoration of the spine (for example). For instance, in some embodiments, the implant may be used to restore and/or expand the distance between two vertebrae (e.g., between two adjacent vertebrae).

In some embodiments, an implant is presented that includes a single plane of expansion, intrinsic to the implant, for instance, a plane of expansion that corresponds to a plane between a two vertebrae.

Some embodiments of the implant may further include at least first and second opposed plates that are intended to move away from one another according to a plane of expansion as the implant is expanded. The at least first and second opposed plates may include first and second bearing surfaces, respectively, where each of such surfaces may further include (or at least one of such surfaces may further include) a recess configured for engaging a portion of one of two surfaces of a bone or a portion thereof.

Some embodiments of the disclosed implant may additionally include at least first and second opposed end members that are associated with each of the opposed plates, where at least one of the end members includes an aperture configured for receiving at least a portion of a retaining element. The retaining element may be moveably associated with one or more of the end members, adapted for retaining the implant, once expanded, in the expanded configuration. Such "retaining" may also be locking, that is, locking the implant in an expanded configuration. Methods of using at least some of the disclosed embodiments enable the alleviation of back pain and/or the restoration and/or treatment of adverse spinal conditions.

BRIEF DESCRIPTION OF THE DRAWINGS

According to common practice, the various features of the drawings may not be presented to-scale. Rather, the dimensions of the various features may be arbitrarily expanded or reduced for clarity. The drawings illustrate various features of at least some of the disclosed embodiments. Included in the drawings are the following figures:

FIG. 3 illustrates a lateral view of the embodiment illustrated in FIG. 1A.

FIG. 4 illustrates a view in section according to the line I-I of FIG. 3.

FIG. 5 illustrates a view in section according to the line II-II of FIG. 3.

FIG. 6A represents an end view according to view F of the embodiment according to FIG. 1A. FIG. 6B represents a side-view of an embodiment of a retaining element comprising a head portion, screw threads and an abutment.

FIG. 7 illustrates a view from above of the embodiment according to FIG. 1A.

DEFINITIONS

Figure 1A:
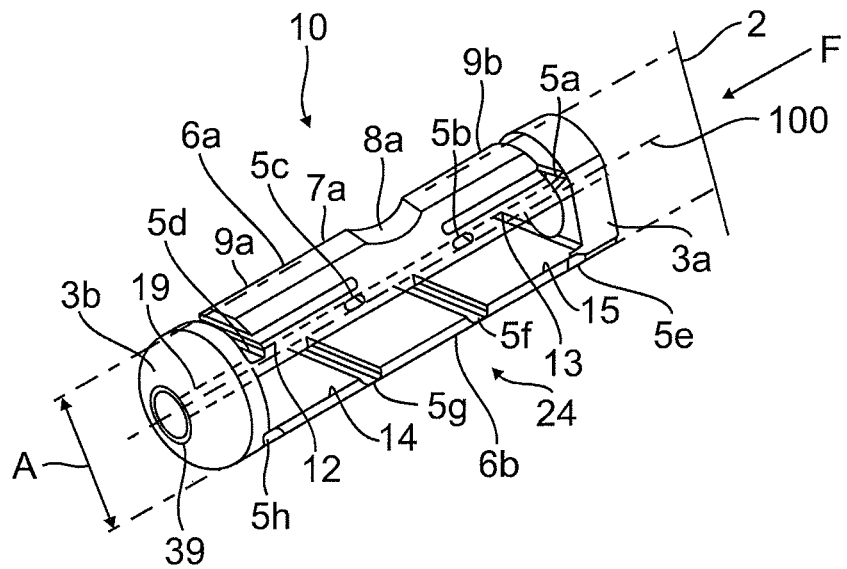
FIG. 1A illustrates a perspective view of an embodiment of an expansible implant according to the disclosure, in a resting position.

Before embodiments of the subject disclosure are further described, it is to be understood that the disclosure is not limited to particular embodiments described, as such may of course vary. It is also to be understood that the terminology used here in is for the purpose of describing particular exemplary embodiments only, and is not intended to be limiting. Unless defined otherwise, all technical terms used herein have the same meaning as commonly understood by one skilled in the art to which this disclosure belongs.

Where a range of values is provided, it is understood that each intervening value, between the upper and lower limit of that range, and any other stated or intervening value in that stated range, is encompassed within at least some of the embodiments of the subject disclosure. The upper and lower limits of these smaller ranges may independently be included in the smaller ranges, and are also encompassed within at least some of the embodiments of the subject disclosure, subject to any specifically excluded limit in the stated range. Where the stated range includes one or both of the limits, ranges excluding either or both of those included limits are also included in at least some of the embodiments of the subject disclosure.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of said publication, published patent application, or patent as prior art.

It must be noted that as used herein and in the appended claims, the singular forms "a", "and", and "the" include plural referents unless the context clearly dictates otherwise. Thus, for example, reference to a "bearing surface" includes a plurality of such bearing surfaces, and reference to "the retaining element" includes reference to one or more retaining elements and equivalents thereof known to those skilled in the art, and so forth.

It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation. Accordingly, the term "optional" or "optionally present"—as in an "optional element" or an "optionally present element" means that the subsequently described element may or may not be present, so that the description includes instances where the element is present and instances where it is not.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

DETAILED DESCRIPTION

At least some of the embodiments of the subject disclosure include an expansible/expandable implant which may be used, according to some embodiments, to restore and/or expand the distance between two vertebrae (e.g., between two adjacent vertebrae).

The implant may include at least first and second opposed plates that are intended to move away from one another according to the plane of expansion as the implant is expanded. The at least first and second opposed plates may include first and second bearing surfaces, respectively, which surfaces may each include a recess configured for engaging a portion of at least one vertebrae (or at least one of the plates/bearing surfaces may include a recess).

The implant may additionally include at least first and second opposed end members that are associated with each of the opposed plates, one or more of which may include an aperture configured for receiving a retaining element (may also be referred to as a locking element). The retaining element may, therefore, be moveably and/or re-movably associated with one or more of the end members, wherein the retaining/locking element may be adapted for at least retaining (and/or locking) the implant, once expanded, in an expanded configuration. Methods of using such expansible implants for the alleviation of back pain and the restoration and/or treatment of adverse spinal conditions are also provided herein.

As summarized above, some of the embodiments of the subject disclosure provide for an expansible implant. In some embodiments, the implants may be employed to either retain or expand the distance between two vertebrae. Such implant embodiments includes a collapsed configuration, suitable for implantation at the spine, and an expanded configuration, for instance, where the implant retains or expands the distance between vertebrae.

In some embodiments, the diameter (or minimal height) of the expansible implant in a collapsed configuration may be between about 5 mm and about 15 mm, for instance, between about 7 mm and about 12 mm, such as between about 8 mm and about 10 mm. Likewise, in some embodiments, the expansible implant may have a maximally expanded diameter/height that ranges from between about 10 mm and about 25 mm, for instance, between about 12 mm and about 20 mm, such as between about 15 mm and about 18 mm.

Further, due in part to the retaining element of the subject implant, the implant may have a variety of configurations that range between a minimally collapsed configuration to a maximally expanded configuration. In this manner, the degree and rate of expansion (and/or retraction) of the implant may be precisely controlled so as to specifically conform to an inter-vertebral space in need of correction. For instance, a suitable height of expansion may range continuously from between about 0 mm and about 25 mm, for instance, between about 5 mm and about 15 mm, such as between about 8 mm and about 10 mm.

According to some embodiments, the implant is used in an intervertebral application, where the implant may be configured so as to be inserted into an intervertebral space between two vertebrae (for example), or inserted between two bone segments of vertebrae (e.g., two adjacent vertebrae). For instance, in some embodiments, such as where there has been a deterioration of the intervertebral disc, an intervertebral implant according to some embodiments may be inserted, in a collapsed configuration into the deteriorated region between two vertebrae and, once appropriately positioned, may be expanded so as to restore or retain the space between the two vertebrae. In some embodiments, the implant is inserted between two spinous processes of adjacent (for example) vertebrae.

As described above, the implant according to some embodiments may have a collapsed configuration and an expanded configuration and may be moveable from the collapsed to the expanded configuration. In some embodiments, the implant in the collapsed configuration includes a tubular body, which tubular body may be manufactured of any suitable material by methods well known in the art. For instance, the body may be fabricated from biocompatible material, for example titanium, into a tubular body using lathe, laser, and/or electro-erosion manufacturing techniques (cast manufacturing may also be used).

Accordingly, in some embodiments, the implant of the subject disclosure may include one or more plates. For instance, in some embodiments, the implant includes a plurality of plates, including at least a first and a second plate in an opposed configuration to one another. A plate of the subject disclosure may have any suitable shape and have any suitable size so long as it is capable of assisting in the engagement and/or support of a body element, such as a bone or tissue. For example, in some embodiments, a suitable plate of the subject disclosure may have a width that ranges from about 5 mm and about 12 mm, for instance, between about 7 mm and about 10 mm, such as between about 8 mm and about 9 mm. In some embodiments, the plate may have a length that ranges from about 10 mm and about 30 mm, for instance, between about 15 mm and about 25 mm, such as between about 18 mm and about 20 mm. In some embodiments, the plate may have a thickness that may range from about 0.2 mm and about 10 mm, for instance, between about 1 mm and about 7 mm, such as between about 2 mm and about 5 mm. In one embodiment, each of a plurality of plates may form partially cylindrical support surfaces, one portion of which may be parallel to a longitudinal axis of the expansible implant.

In some embodiments, the length of the implant may be sized to be substantially equal to the plate(s) and/or a support surface thereof. Such a feature allows optimization of a ratio of the support length on the bone, tissue, or other body element to the length of the implant. As will be described in more detail below, in some embodiments, a filling material may be injected in and/or around the implant after it has been expanded. An injection pressure of such a filling material is preferably low so as to avoid having the filling material be injected into inappropriate tissues such as blood vessel walls (or out of an intravertebral body, for example).

Such a material may be a filler cement (or in some embodiments may be a silicone or any biocompatible soft or hard material) which may aid/assist in compressive load with the implant. Cements that may be used with the implants may include an ionic cement, in particular a phosphocalcic cement, an acrylic cement, a compound of the latter, and or any other suitable cement well known in the art.

In some embodiments, the plates of the implant include or act as a bearing surface (e.g., external, tissue-engaging surface of a plate) configured for engaging a bone, tissue, or other body element of a subject (i.e., patient), such as a vertebral bone or vertebral or intervertebral tissue. In some embodiments, the plate/bearing-surface includes a recess, notch, and/or opening ("engaging member") which receives a portion of the bone or tissue to which the implant is placed. Accordingly, in some embodiments, the engaging member (e.g., recess, etc.) has a morphology that is complimentary to a bone, tissue, or other body element so as to receive and/or engage the bone, etc. in a snug and/or predetermined manner.

For example, in some embodiments, the bearing surfaces each include an engaging member that is configured for engaging a portion of a respective vertebra of two vertebrae adjacent each respective plate. In some embodiments, the bearing surface of the plates include an extended, elongate or winged portion.

The engaging member may have any suitable shape and/or dimension so as to receive or otherwise engage a bone, tissue, or other body element. For instance, the engaging member may be round, spherical, square-like, V-shaped, parabolic, concave, convex and/or the like. Specifically, in some embodiments, the engaging member is configured as a recess, which may have a width that ranges from about 2 mm and about 12 mm, for instance, between about 4 mm and about 10 mm, such as between about 5 mm and about 6 mm. In some embodiments, the engaging member may have a length that ranges from about 5 mm and about 12 mm, for instance, between about 7 mm and about 10 mm, such as between about 8 mm and about 9 mm. In some embodiments, the engaging member may have a depth that ranges from about 2 mm and about 10 mm, for instance, between about 4 mm and about 8 mm, such as between about 5 mm and about 6 mm.

In some embodiments, the implant may include two opposed plates with first and second bearing surfaces, where at least one (and preferably both) first and second bearing surfaces each include a recess, notch, etc. configured for engaging at least a portion of a restoration surface, such as a bone, tissue, or other body element surface of a subject. Accordingly, the implant may be expanded by the movement of a first and second opposing plate away from one another, when the implant is opened out. Such a feature allows the pressure which is exerted by the bearing surface of the plates of the implant on the bone, tissues, etc. to be reduced, for instance, by increasing the contact or support surface.

In some embodiments, the implant may include one or more end members, which may be integral with the implant. For instance, in some embodiments, the implant includes a plurality of end members, such as at least a first and a second end member in an opposed relationship and spaced apart from one another.

An end member in some embodiments may have any suitable shape and any suitable size so long as the end member is capable of associating with one or more of a plate and/or end member so as to facilitate the expanding, contracting, and/or retaining of the expansible implant into a desired configuration. For example, an end member may be round, circular, triangular, pyramidal, square, etc. In some embodiments, a suitable end member of the subject disclosure may have a width or diameter that corresponds to the width or diameter of the implant, and such width/diameter may be within a range of about 5 mm and about 15 mm, for instance, between about 6 mm and about 12 mm, such as between about 8 mm and about 10 mm. In some embodiments, each end member may have a length that ranges about 1 mm and about 5 mm, for instance, between about 2 mm and about 4 mm, such as about 3 mm. In some embodiments, the end member may have a thickness that may range from about 0.5 mm and about 5 mm, for instance, between about 1 mm and about 4 mm, such as between about 2 mm and about 3 mm.

In some embodiments, the implant includes a plurality of opposed end members that are associated with both a plurality of opposed plates and a retaining element, which together are configured such that as the end members are drawn together (e.g., the distance between the end members decreases longitudinally), the implant expands in a direction perpendicular to a longitudinal axis of the implant. In some embodiments, such expansion may be radial e.g., within a single plane of expansion.

In some embodiments, the end member includes an aperture, such as an aperture configured for receiving a portion of a retaining element. For instance, in some embodiments, the end members includes an aperture configured for receiving one end of a retaining element. Specifically, in some embodiments, the end member includes a proximal surface and a distal surface and includes at least a first aperture provided therein, wherein the aperture extends there through from the proximal surface to the distal surface. In some embodiments, the aperture includes a mating area, which may include a mating surface, where the mating area is configured for mating with a respective mating portion of a retaining element.

An aperture of an end member may be of any suitable shape and of any suitable size, so long as it is configured so as to receive a retaining element and/or snugly fit a retaining element there through. Such apertures may include screw threads which correspond to screw threads of a retaining member. For instance, in some embodiments, the aperture is circular or round and includes a diameter that ranges from about 1 mm and about 6 mm, for instance, between about 2 mm and about 5 mm, such as between about 3 mm and about 4 mm. It is worth noting that one or both end members may include apertures with mating areas, e.g., threading, therein. For example, where the retaining element may be an elongated, shaft member that includes a mating surface that includes threading, the apertures of both end members may include threading, or the aperture of only one end member (e.g., distal end member) may include threading.

Where the retaining element is elongated, including a shaft (for example, a solid or tube-like shaft) having threading on its distal end portion, the aperture of the distal end member may include corresponding threading. To that end, for example, where a distal end of a retaining element containing threading is inserted through an aperture in the proximal end member (the aperture of the proximal end member may or may not include screw threads) and into the aperture of a distal end member, where the distal end member includes threading that corresponds to the threading on the distal portion of the retaining element. In this example, the retaining element also includes a proximal portion which may include an abutment, which in some embodiments, corresponds to the head of a screw, and more particularly, to the underneath side of the head of a screw. The length of the retaining element, in such embodiments, may correspond initially to the length of the implant (i.e., from end member to end member).

In such a configuration, the retaining element is enabled to retain the implant in an expanded configuration with the distal end portion of the retaining element being screwed into the distal end member, and the underneath side of the screw head located on the proximal portion of the retaining element abutting the outer proximal surface of the proximal end member. In some embodiments, the retaining element may also act as a expansion mechanism for the implant. Using the same example above, according to some embodiments, the implant is held in place (e.g., through either an installation tool, bone and/or other bodily tissue), and the threads of the distal end portion of the retaining element engage the threads of the aperture of the distal end member. Upon insertion the underneath side of the head of the retaining member comes into contact with the outer proximal surface of the proximal end member, thus, upon expansion the head of the retaining element applies a force as the retaining element is screwed into the distal end member, where such force causes the implant to expand, and in some embodiments, shorten in length as the implant is expanded. In this and other such manners, the expansion and the degree of expansion of the implant may be controlled by the amount of threaded engagement of the corresponding screw threads.

The threading of an aperture of an end member and/or the threading of the retaining element may have any suitable pitch, so long as the pitch is capable of being associated with an end member and/or retaining element. For instance, a suitable pitch for the threading of an end member and/or retaining element may be from about 0.25 mm and about 3 mm, for instance, between about 0.5 mm and about 2.5 mm, such as between about 1 mm and about 2 mm.

Further, in some embodiments, the proximal and/or distal surface of the end member may further include a recess, such as a recess configured for receiving a portion of a retaining element. Specifically, in some embodiments, the proximal surface of an end member includes a recess, wherein the recess surrounds an aperture and is configured for receiving the proximal portion of a retaining element such that when a distal portion of the retaining element is fully received within the aperture, the proximal portion of the retaining element (e.g., the head portion) does not extend beyond the bounds or plane of the proximal surface of said end member. Rather, the head portion of the retaining element aligns within the recess so as to be flush with the proximal surface of the end member.

In some embodiments, the one or more surfaces of the end member may include a recess or notch region containing a notch element, such as a notch that is adapted to engage and/or otherwise receive a portion of an implantation installation device, such as an implant holder.

In some embodiments, an expansible implant includes one or more supports for one or more of the plates and/or one or more material webs or plastically deformable zones. One or more such webs/zones may be associated with one or more supports. For instance, in some embodiments, the implant includes a plurality of supports, such as at least a first and a second support, which support may be directly or indirectly associated with a plate, and/or bearing surface thereof, and/or an end member(s). For example, in some embodiments, an expansible implant includes first and second plates that include first and second bearing surfaces, where the implant additionally includes first and second supports that are associated with each of the first and second plates and/or bearing surfaces thereof. In some embodiments, the first and second supports are further associated with first and second end members. In some embodiments, the first and second supports comprise a plurality of first and second supports.

In some embodiments, the implant includes first and second supports for each of the first and second bearing surfaces of the plates, wherein the supports are positioned under each plate, respectively. In some embodiments, the opening out of the first and second plates includes the raising of the plates via the use of the one or more supports positioned under the plates. Such a feature may allow thrust forces to be distributed under the plate in order to reduce the cantilever.

A support of the implant may be of any suitable dimension so long as it is capable of being associated with one or more of a plate and an end member, and in some embodiments, either directly or indirectly associating the support with the end member, and thereby serving the purpose of supporting a plate of the implant. Specifically, in some embodiments, a suitable support of the subject disclosure may have a width that ranges from about 5 mm and about 12 mm, for instance, between about 6 mm and about 10 mm, such as between about 8 mm and about 9 mm. In some embodiments, the support may have a length that ranges about 5 mm and about 12 mm, for instance, between about 6 mm and about 10 mm, such as between about 8 mm and about 9 mm. In some embodiments, the support may have a thickness that may range from about 0.2 mm and about 2 mm, for instance, between about 0.5 mm and about 1.5 mm, such as between about 1 mm and about 1.25 mm.

In some embodiments, where a plurality of supports are associated with a plurality of plates, the supports may all have the same length or be of one or more different lengths. For instance, the plurality of supports may have substantially equal lengths, or alternatively, at least one of a first and second support is shorter in length to a corresponding support, such that upon expansion of the implant, the first and second supports move at an angle toward one another.

The material web(s) or zone(s) as briefly described above, are used to control expansion of the implant. The material web/zone may have any suitable configuration so long as it is capable of facilitating the association of a support with a plate and/or end member and is adapted for being deformed, for instance, plastically, so as to control the expansion of the implant. Accordingly, in some embodiments, the material web controls the expansion of the implant by deforming in a predetermined manner to a predetermined extent.

In some embodiments, the material web/zone is an articulation area formed by the thinning of a wall that is interposed between a support portion and a plate and/or end member. Accordingly, the material web may be formed by the production of a weakened zone at a region of connection between a support and a plate and/or end member, for instance, by fabricating a groove in the support material the thickness of which is determined by the depth of the groove, whereby the weakened zone allows the articulation and/or support to be plastically deformed without breaking.

In some embodiments, the material web is positioned between each support and a corresponding plate and/or end member, where the material web includes a predetermined thickness which controls the expansion of the implant. As stated earlier, Accordingly, in some embodiments, the web/zone corresponds to an expansion controlling element(s) for controlling a determined expansion value of the implant, between a minimum height/diameter of the implant before any expansion and a maximum height/diameter of the implant after its maximum expansion.

The retaining element according to some embodiments, may have any suitable shape and any suitable size so long as the retaining element is capable of interacting with one or more of an end member(s) and/or plate(s) of the implant to facilitate the expanding, contracting, and/or retaining (and may include locking of the implant) of the implant into a desired configuration. For example, an retaining element may be an elongate member that may be round, circular, triangular, pyramidal, square, etc. It may be tubular or solid, or a combination thereof. Specifically, in some embodiments, a suitable retaining element of the subject disclosure may be configured as a screw, rivet, cable, wire, and combinations thereof or the like.

For instance, a suitable retaining element may have an extended rivet or screw like configuration, where the retaining element includes an extended body with a proximal portion, a distal portion and a extended body there between. The proximal and/or distal portions may be configured for engaging and/or moveably associating with one or more end members and the extended body may be configured for passing through an aperture(s) in the implant.

In some embodiments, the proximal and/or distal portions of the retaining element may include an abutment and/or a mating area with a mating surface, wherein the abutment and mating areas of the retaining element are configured for being associated with corresponding mating areas of end members and/or the apertures thereof. For instance, as disclosed above, in some embodiments, a proximal or distal portion of a retaining element may include an abutment, wherein the abutment is configured for associating with an end member, for example, an exterior side of a proximal end member. In some embodiments, a proximal or distal portion of a retaining element may include a mating area, wherein the mating area is configured for associating with a corresponding mating surface of an end member, for example, a corresponding mating area of an aperture positioned within the end member. Such mating areas may be corresponding screw threads, and may also be a rivet-like configuration.

In some embodiments, the retaining element has an elongate body that has a diameter that ranges from about 1 mm and about 6 mm for instance, between about 2 mm and about 5 mm, such as between about 3 mm and about 4 mm. In some embodiments, the elongate body of the retaining element may have a length that ranges from about 10 mm and about 30 mm, for instance, between about 15 mm and about 25 mm, such as between about 18 mm and about 20 mm.

In some embodiments, the retaining element has an extended wire-like configuration, where the wire may include a proximal portion with a proximal end, a distal portion with a distal end, and an elongate body portion extending between the proximal and distal portions. A distal portion, e.g., a distal end, of the wire may include a retention member, such as a hook like configuration or screw, where the hook is adapted for engaging at least a first portion of a first aperture (located on the distal end member of the implant) such that upon the implant being expanded to a desired expanded state an abutment may be formed on a proximal end of the wire.

In some embodiments, an expansible implant may include one or more envelope members. For instance, the implant may include an expandable envelope member comprising a balloon element that is adapted for at least partially or fully covering the implant (e.g., the implant is "enveloped" within the balloon).

In some embodiments, the envelope member is capable of being expanded by the expansion of the implant from a collapsed to an expanded configuration. In some embodiments, the envelope member is configured for being expanded or further expanded by the insertion of a fluid or material, e.g., a fluid of particulate matter. The envelope member may be fabricated by means known in the art and may be fabricated from any suitable material, such as, for example, silicon, polymers, and the like.

An envelope member, e.g., balloon element, according to some embodiments, may have any suitable size and/or any suitable shape, so long as the envelope member is configured for containing one or more (or all) of the components of the implant. For instance, in some embodiments, the envelope member may attach to a plate, for instance, a bearing surface or a recess therein of the implant. In some embodiments, the envelope member may attach to at least one end member of the implant. In some embodiments, the envelope member is of a size and shape to contain the implant entirely within the envelope/balloon and the balloon may be expanded around the implant.

In some embodiments, the envelope member may be configured so as to have a specific contour that allows the envelope member to engage a specific bone portion with a predetermined morphology. For instance, when the implant and envelope are both in an expanded configuration, both the envelope and a recess of the implant may engage a portion of a vertebral bone thereby fixing the implant between one or more vertebral bones of the spine.

As summarized above, the expansible implants of the present disclosure are useful for restoring vertebral bone anatomy either within a deteriorated vertebral body or between vertebral bodies. Reference will now be made in detail to various embodiments of the disclosure, which are illustrated in the accompanying figures.

Referring now to FIGS. 1-7, the expansible implant 10 represented therein may include one or more of the following: an expansion plane 2, which may be intrinsic to the implant; an end member(s) (e.g., 3a and 3b), which end member(s) may be used for positioning the expansible implant between two surfaces and facilitating the expansion of the implant along a plane of expansion between the two surfaces; a first and/or second plate(s) (e.g., 6a and 6b), which plate(s) is configured for moving axially away from a central (e.g., longitudinal) axis defined by line 100, and may include a bearing surface 7a and/or a recess 8a and/or extended e.g., winged, portions 9a and 9b, wherein the recess 8a may be configured for engaging a portion of a restoration surface, which may be a portion of a bone. A support(s) (e.g., 12, 13, 14, and 15), may be associated with one or more of a plate or end member, and may be configured for assisting in the opening out (i.e., expanding) of the expansible implant in the expansion plane 2. A material web or plastically deformable zone/area (e.g., 5a, 5b, 5c, 5d, 5e, 5f, 5g, and 5h), for at least partially controlling expansion of the implant, e.g., controlling expansion to a determined expansion value, between a minimum thickness/diameter A of the implant before expansion of the implant and a maximum thickness/diameter B of the implant after its maximum expansion. A retaining element (e.g., 19), may be associated with one or more end members, wherein the retaining element is adapted for retaining the implant in an expanded configuration once expanded. As illustrated in FIGS. 1A and 1B, first 6a and a second 6b opposite plates include/form first 7a and second 7b bearing surfaces which are intended to be moved apart one from the other along the expansion plane 2 during expansion of the implant 10.

Figure 1B:
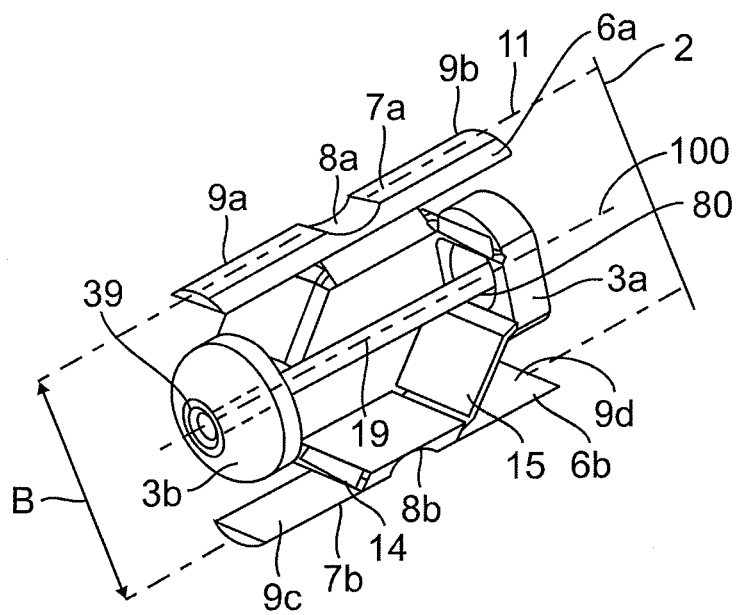
FIG. 1B illustrates the example of FIG. 1A, in opened-out position.

As shown in FIGS. 1A and 1B, implant 10 may include a cylindrical shape with a transverse circular exterior section. The implant 10 may include first 3a and second 3b ends which adopt the shape of a transverse section of the tubular (for example) body 24. The ends are preferably moveable and may be brought towards one another to allow the opening-out/expansion of the implant, as represented in FIGS. 1B and 2B. Accordingly, the two ends 3a, 3b may be associated with each other by one or more of a material web/zone/area 5, support(s) 12-15, plate(s) 6, and/or retaining element 19. For instance, ends 3a and 3b may be associated with one another either directly or indirectly via a plurality of opposed plates 6a and 6b, which plates may be parallel to central axis 100 when the implant is unexpanded and formed longitudinally in the tubular body 24. Further, the plates may be coupled with supports 12-15, which supports may be interposed between the plates and the ends and may be configured to be folded under the plates thereby functioning in part to bring the ends 3a and 3b towards each other, while distancing the first 6a and second 6b opposite plates from the longitudinal axis 100 of the tubular body 24.

Figure 2A:
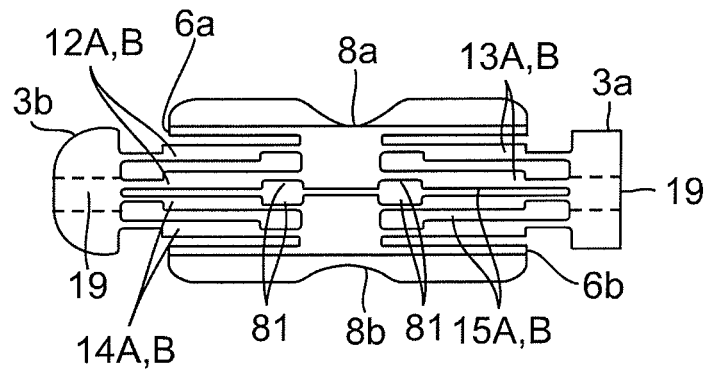
FIG. 2A illustrates a side view of an embodiment of an expansible implant according to the disclosure, in a resting position.
Figure 2B:
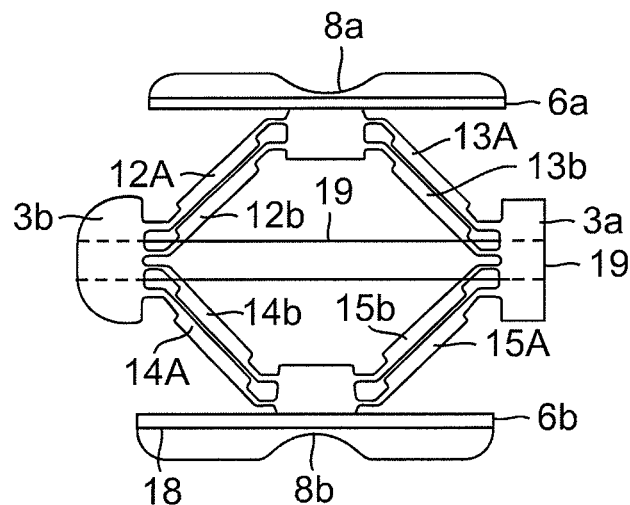
FIG. 2B illustrates the example of FIG. 2A, in opened-out position.
Figure 2C:
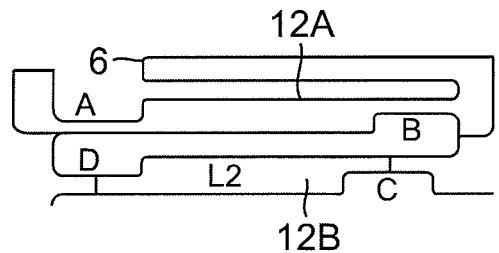
FIG. 2C illustrates an enlarged side view of support members for the embodiment illustrated in FIGS. 2A and 2B.

FIGS. 2A-2C illustrate an embodiment of the implant which is similar to the embodiment disclosed in FIGS. 1A and 1B, but with an additional set of supports (e.g., a four bar linkage). More specifically, the implant in FIGS. 2A-2C includes supports 12A, 12B, 13A, 13B, 14A, 14B, and 15A, 15B. The additional supports may provide further rigidity for the implant and/or may insure that plates 6a and 6b, which plates include recess 8a and 8b, open-out in a substantially parallel and/or even manner.

As represented in FIGS. 4-5, in order to allow the plates 6a and 6b to be opened out in an expansion plane 2 (passing through the longitudinal axis 100 of the tubular body 24), the plates 6a and 6b may be diametrically opposed. For instance, the plates 6a and 6b may be formed from a transverse recess 40 of the tubular body 24, traversing the tubular body throughout, and extending over the length of the tubular body between the two ends 3a and 3b of the implant 10. As represented in FIG. 5, the plates 6a and 6b connecting the two ends 3a and 3b, respectively adopt a transverse section bounded by a circular arc 26 of the exterior surface of the tubular body 24. Chord 27 defines the circular arc 26 and may be included in the wall 25 to form recess 40. The recess 40 may be symmetrical with respect to the longitudinal axis 100, as illustrated, retaining element 19 resides in recess 40. Further, plates 6a and 6b include recesses 8a and 8b, respectively.

With respect to FIG. 3, each plate 6a and 6b may be divided into three successive rigid parts, which may be articulated together in conjunction with the ends 3a and 3b, in some embodiments, as follows. With respect to the upper plate 6a, a first rigid support 28 is connected at one end to end 3a by means of an articulation, e.g., material web/zone 29. The other end of rigid support 28 is connected to a first end of a second adjacent rigid part 30 of plate 6a by means of an articulation, e.g., material web/zone 31. The second rigid part 30 of plate 6a may be connected at a second end to a second rigid support 32 by means of an articulation, e.g. material web/zone 33. The other end of the second rigid support 32 may be connected to end 3b by means of an articulation, e.g., material web/zone 34. In some embodiments, the articulations 29, 31, 33 and 34 may include one degree of freedom in rotation, acting, respectively, about axes which are perpendicular to the expansion plane 2. Further, articulations 29, 31, 33 and 34 may be formed by a thinning of the wall forming the member in the relevant articulation zone, as represented in FIGS. 1A-3 (see, e.g., reference numerals 5 and 81).

Plates 6a and 6b may also include a recess 8a and 8b respectively, wherein the recess is configured for engaging a portion of a bone and/or a restoration surface. Additionally, a retaining element 19, spans the implant and may be moveably associated with ends 3a and 3b, such that as the retaining element is engaged, ends 3a and 3b are moved toward one another, longitudinally along central axis 100, thereby causing articulations 29, 31, 33 and 34 to fold under plates 6a and 6b and thereby causing plates 6a and 6b to move axially away from central axis 100 and away from one another along an expansion plane 2, thereby causing the implant to expand, as depicted in FIGS. 1B and 2B.

Each plate 6a and 6b may open out such that the recesses 8a and 8b move away from the longitudinal axis 100 of the implant pushed by the adjacent rigid supports (e.g., 28, 32, 42, and 44), when the ends 3a and 3b of the implant are brought one towards the other, and in some embodiments, by effectuation of the retaining element 19. As represented more particularly in FIG. 3, in order to initiate the movement of the plates in the correct direction when the ends 3a and 3b are brought towards the other, a suitable rotation couple of the various parts of the plate/support may be established.

Rigid supports 28, 32,42, and 44, associated with upper and lower plates 6a and 6b, respectively, may be articulated on ends 3a and 3b, respectively, in the lower part of the material web/zone associated with these rigid supports. The rigid parts of supports 28, 32 may also be articulated in their association with central rigid part 30 of plate 6a in an upper part of the material web which forms rigid parts 28, 32. The same may be true (according to some embodiments) for the corresponding elements of the lower plate 6b. The displacement of the articulations establish a rotation couple (for example) on the rigid parts of supports 28 and 32, when a force is applied to bring the ends 3a and 3b together along the longitudinal axis 100 of the implant. This displacement tends to make the rigid supports 28 and 32 pivot away from the longitudinal axis of the implant as a result of moving the central rigid part 30 and recess 8a away from the longitudinal axis 100. The same holds for the elements of lower plate 6b, which may be constructed in a similar manner as the upper plate and may be symmetrical to the upper plate 6a with respect to a plane which is perpendicular to the expansion plane 2 passing through the longitudinal axis 100.

Thus, according to some embodiments of the present disclosure, the articulations of the upper 6a and lower 6b plates may be formed by weakened web/zones/areas produced by grooves 81. The grooves define the thin material web/zone forming the tubular body 24, the thickness of which may be determined by the depth of the grooves 81 (as represented in the figures) in order to allow elastic deformation and/or plastic deformation of the material web/zone/area without breaking. Specifically, the rigid parts of supports 28 and 32 of the upper plate 6a, and their symmetrical zones on the lower plate 6b, e.g., 42 and 44, can adopt a position, termed extreme expansion, in which the intended rigid supports are perpendicular to the longitudinal axis 100 of the implant 10, when the ends 3a and 3b are brought one towards the other such that the implant is opened up until its maximum expansion capacity, resulting in elastic deformation and/or plastic deformation of the corresponding web material. The width of the grooves 81 may be pre-determined to allow such a clearance of the parts of the upper and lower plates and also to impart a suitable radius of curvature to the webs in order to ensure elastic deformation and/or plastic deformation without rupture of the material.

The first 9a and second 9b elongate or wing portions of plate 6a and first 9c and second 9d elongate or wing portions of plate 6b may be formed coextensively in the upper 6a and lower 6b plates. With respect to the upper plate 6a, for example, rigid wing portions 9a and 9b may be formed by the central rigid part 30 of plate 6a and by material extensions extending out both sides thereof. In order to produce the rigid wing portions 9a and 9b, supports 28 and 32 may be separated from the upper plate 6a using a pair of transverse slots 35 and 36 which extend longitudinally over the length each respective support (see FIGS. 3-4). Articulations 31 and 33 and supports 28 and 32 form, respectively, a first and a second support for the first 6a plate. The same applies to the second plate 6b by symmetry.

Hence, the first 6a and second 6b plates may comprise respectively a first 9a, 9c and a second 9b, 9d cantilever wing, the respective attachment zones of which are situated at the level of the first and second supports. As represented in FIGS. 1A-3, the first 9a, 9c and second 9b, 9d cantilever wings may include a length corresponding substantially to the maximum displacement value of one of the first 6a or second 6b plates in an expansion plane 2. It is to be noted that the wings may, in some embodiments, be longer than the maximum displacement value, although such may not be seen in FIGS. 1-3.

The first 6a and second 6b plates form first 7a and second 7b bearing surfaces, respectively, each having a length which may be substantially equal to the length of the implant and which may be displaced perpendicularly to the longitudinal axis 100 during expansion. The first 7a and second 7b bearing surfaces may each include a recess 8a and 8b, respectively, wherein the recess may be configured so to engage and/or support a portion of a bone, tissue, or other body portion, for instance, along a plane of expansion between two surfaces, e.g., bone portions. According to some embodiments of the disclosure, since the implant 10 is formed in a tubular body 24, the first 6a and second 6b plates form, respectively, curved support surfaces, which include a recess, and are parallel to the longitudinal axis 100.

One or more of the end members 3a and 3b may include a positioning element which may be a configuration suitable for positioning the expansible implant in a bone or between bones and which facilitates and/or allows the expansion plane 2 to correspond with a space between two bones in need of restoration, and in particular, in need of spatial/distance restoration, and may include an engagement mechanism which allows for the angular orientation of the implant about longitudinal axis 100. For example, such configuration may include one or more flat surfaces (e.g., 37 and 38) or other anti-rotational design (e.g. cross, square shape, hexagonal shape, central or non-central groove, and the like) which are formed on the cylindrical surface with a circular section of end 3a, which may allow for rotational engagement of the implant 10.

An expansion element for causing the opening out of the expansible implant in an expansion plane 2, may include a configuration that includes end supports 28 and 32 of upper plate 6a and the corresponding symmetrical supports on the lower plate 6b, allowing opening out of the plates. A retaining element 19 (which may also be considered an expansion element used to expand the implant) may be used to allow the ends 3a and 3b of the implant to be brought together when placed in an implant position between two restoration surfaces. For instance, a retaining element 19 may be included where the retaining element includes a proximal and distal ends as well as an elongate portion there between. The retaining element 19 may be moveably associated with ends 3a and 3b such that as when the retaining element is engaged, the ends of the implant are brought one to another. For example, the retaining element 19 may include one or more threaded portions, e.g., on one or more of its proximal or distal ends, which threaded portions correspond to threaded portions within an aperture of the end members, wherein as the retaining element is rotated the corresponding threads cause one or more of the end members 3a and 3b to move axially along the retaining element 19 so as to be brought together, thereby causing the implant to expand. As other example the retaining element 19 and/or the end members 3a and 3b may include one or more lip/circular tooth on one or more of its proximal or distal ends. In such an embodiment, when the retaining element 19 is pulled it causes 3a and 3b to move axially along it, causing the implant to expand. The corresponding lips block the end members into position and maintain the expansion.

Alternatively, an implant carrier may be provided wherein the implant carrier, by being supported on the end 3a, for example, allows the end 3b to be pulled toward end 3a, or by being supported on end 3b, end 3a is pushed toward end 3b. To this end, the distal end 3b, for example, comprises an aperture or opening 39 that is threaded along the longitudinal axis 100 in order to allow the engagement of the implant carrier, which includes a corresponding threaded portion. The proximal end 3a may include a bore 80 along the longitudinal axis 100 in order to allow the passage of a core of the implant carrier as will be explained further on. A suitable carrier tool may be one such as described in U.S. Application Publication No. 2006/0004455 to Leonard, et al., hereby incorporated herein in its entirety.

The retaining element, when performing as an expansion element, may also allow the implant to be expanded to a desired expansion—i.e., if the retaining element is a screw-like device, the number of turns of the retaining element may correspond to a predetermined height of the expanded implant. Additionally, a control configuration may be provided by the articulations 29, 31, 33, 34, etc., wherein the thickness of the material webs defining the articulations are capable of deforming in the plastic region, e.g., 81, so as to allow the expansion of the plates of the implant to substantially preserve a determined opening-up position of the plates, apart from elastic shrinkage which is negligible in practice.

The expansion of the plates 6a and 6b of the implant, and their stabilization once opened up, can be achieved through adaptation of the recesses 8a and 8b in plates 6a and 6b, respectively, to the bone geometry. Further, in some embodiments of the disclosure, the implant 10 allows a non-parallel displacement of plates 6a and 6b and, at the end of the displacement, allows a definitive position of the plates in a non-parallel state if necessary (e.g., as a function of the bone anatomy). For example, the expansion of plates 6a and 6b may be non-parallel if the lengths of individual supports (e.g., 12 and/or 13, etc.) are of different lengths. For example, if supports 12 and 14 are longer than supports 13 and 15 (see FIGS. 1A-2B), opening out the implant will force plates 6a and 6b to angle away from each other. In FIGS. 1A-2B, this would result that plates 6a and 6b at end 3b to be further apart from one another then at end 3a. As one of ordinary skill in the art will appreciate, depending upon the configuration, only one respective support need be lengthened/shortened, to obtain a particular angle.

Similarly, as shown in FIGS. 2A-2C, when the four bar linkage comprising supports 12A, 12B, 13A, 13B, 14A, 14B, 15A, 15B, as shown, are equal lengths (i.e., length of 12A=length of 13A, length of 12B=length of 13B, etc.), a parallelogram is then created upon expansion of the implant, which ensures parallelism between segments AD and BC (FIG. 2C). By modifying the lengths of L1 and L2, the four bar linkage is no longer a parallelogram, but rather an angle between plate 6a and 6b occurs. The angle formed may also be dependent on how close ends 3a and 3b are drawn near to each other. As the implant is opened-out, the angle slowly increases.

FIGS. 8-16 relate to additional embodiments of an expansible implant 101, the elements of which are preferably functionally similar to the corresponding elements of the implant embodiment illustrated in FIGS. 1-7. Moreover, the corresponding features in FIGS. 8-16 relating to the embodiment illustrated in FIGS. 1-7 include the same reference numerals, respectively, with the addition of the number 100 and therefore will not be described further.

Figure 8:
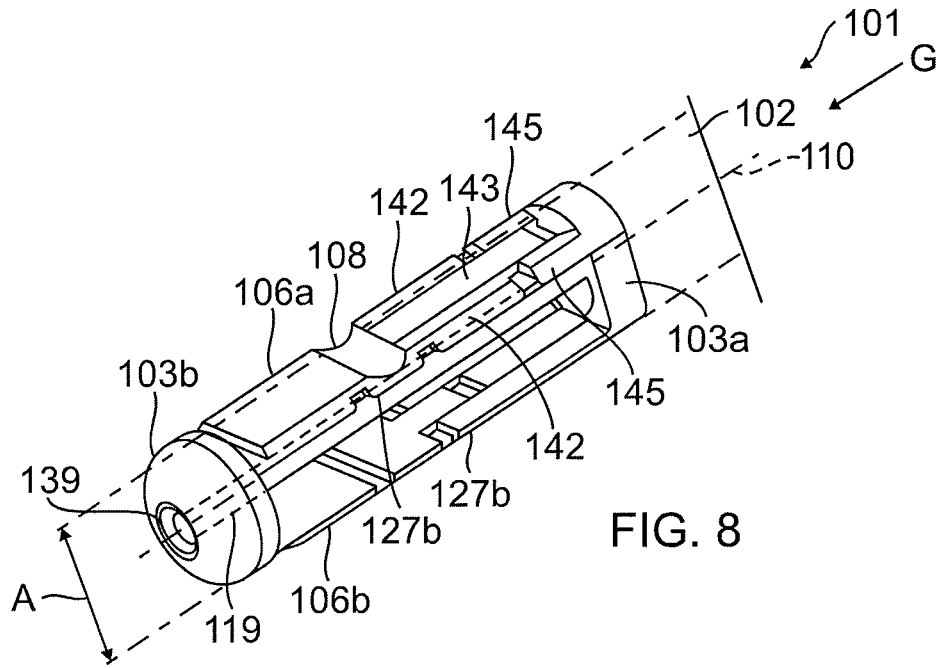
FIG. 8 illustrates a perspective view of another embodiment of an expansible implant according to the disclosure, in a resting position.
Figure 9:
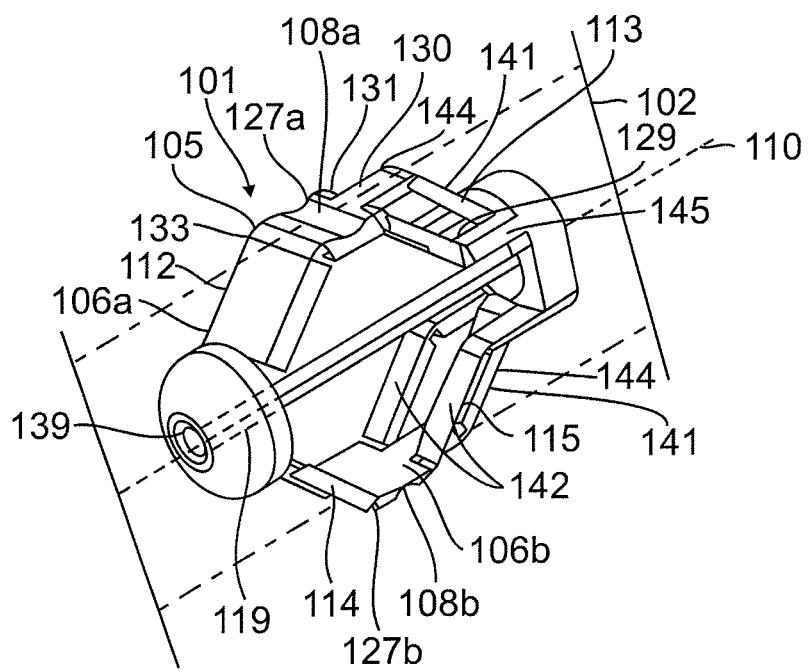
FIG. 9 illustrates the example of FIG. 8, in opened-out position.
Figure 10:
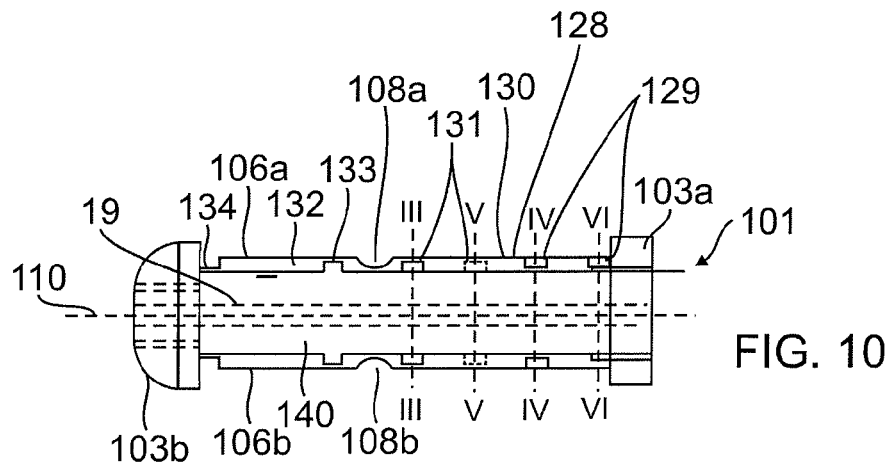
FIG. 10 illustrates a lateral view of the example according to FIG. 8.
Figure 11:
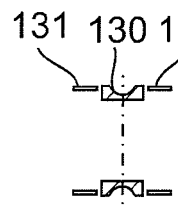
FIG. 11 illustrates a view in section according to the line III-III of FIG. 10.
Figure 12:
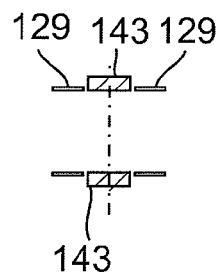
FIG. 12 illustrates a view in section according to the line IV-IV of FIG. 10.
Figure 13:
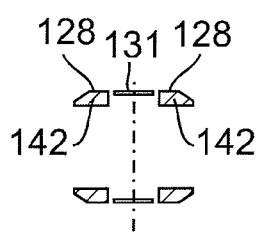
FIG. 13 illustrates a view in section according to the line V-V of FIG. 10.
Figure 14:
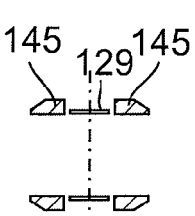
FIG. 14 illustrates a view in section according to the line VI-VI of FIG. 10.
Figure 15:
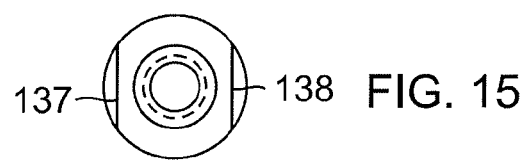
FIG. 15 illustrates an end view according to direction G of the example according to FIG. 8.
Figure 16:
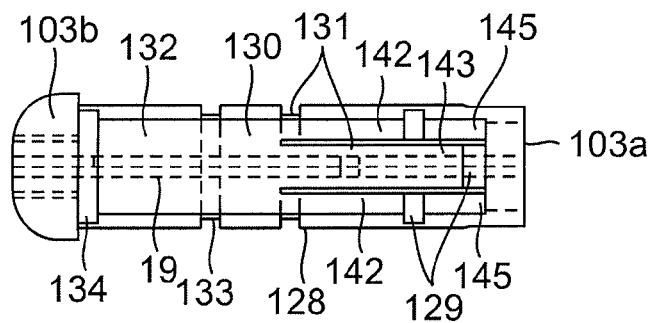
FIG. 16 illustrates a view from above of the embodiment according to FIG. 8.

The represented implant 101 differs from the implant 10 by the absence of the wing portions (e.g. 9a, 9b, 9c and 9d) on the plates 106a and 106b, as represented more particularly in FIGS. 8 and 9. Implant 101 is illustrated to include (but not limited as such) a parallelogram system 141 on one of the end parts of support 128 or 132 of each of the plates 106a and 106b. In the illustrated example, the parallelogram system is represented on support end part 128 of upper plate 106a, connected to the end 103a and the corresponding system on lower plate 106b. The parallelogram systems may be used to ensure displacement of the plates 106a and 106b, parallel to longitudinal axis 110 of the implant 101. As represented in the figures, the support end part 128 of the plate 106a (similarly on corresponding plate 106b) is split, as are articulations 131 and 129 (respectively) over the central part 130 and over the end 103a of the implant in order to form a parallelogram which is deformable during displacement of the corresponding plate. As illustrated in FIG. 9, the implant 101 additionally includes supports 112, 113, 114, and 115. The supports 112-115 may provide further rigidity for the implant and/or may insure that plates 106a and 106b, which plates include recess 108a and 8b, open-out in a substantially parallel and/or even manner.

A control configuration 105 may also be provided. The control configuration may also be made of other articulations. The articulations of the deformable parallelogram 141 may be produced in the same manner as the other articulations 129, 131, 133, 134 of the plate 106a, as represented in FIGS. 8-16. The disclosed geometry as explained above, and represented in FIGS. 11-14, establishes force couples on the various support parts 128, 130, 132 of the support. This allows for the desired displacements when bringing together ends 103a and 103b of the implant 101.

In order to obtain a deformable parallelogram 141, the support end part 128 of the support is preferably divided into three longitudinal levers: two lateral levers 142 and a central lever 143, which form two sides of the deformable parallelogram 141. The two remaining sides of the parallelogram may be formed by an extension 144 of the central part of the plate 106a, placed in an axis of extension of the central lever 143, and by a double extension 145 of the end 103a, extending parallel to the longitudinal axis 110 of the implant and placed in the axis of extension of the two lateral levers 142 (see FIG. 8).

It is worth noting, that plates 106a and 106b may be symmetrical with respect to a plane which is substantially perpendicular to the plane of expansion 102 passing through the longitudinal axis 110 of the implant 101 in order to obtain, during the expansion of the implant, the displacement of the two plates in a manner parallel to the longitudinal axis 110.

The opposed plates 106a and 106b may also include first 127a and second 127b bearing surfaces, which may each include a recess 108a and 108b, respectively, wherein the recess may be configured so to engage and/or support a portion of a bone, tissue, or other body portion, for instance, along a plane of expansion such as a plane between two bone surfaces. A retaining element 119 may also be included so as to facilitate the expansion of the implant and/or retain or maintain the implant in an expanded configuration once expanded. For instance, a retaining element such as an elongated screw, rivet, or wire may be inserted through an aperture, e.g., 139, in one or both end members 103a and 103b.

The retaining element 119 may associated with the end members and/or plates such that the retaining element may be used to allow the ends 103a and 103b of the implant to be brought together when placed within an implant position between two restoration surfaces. For instance, a retaining element 119 may be included where the retaining element includes a proximal and distal ends as well as an elongate portion there between. The retaining element 119 may be moveably associated with ends 103a and 103b such that as the retaining element is engaged, the ends are brought one to another. For example, the retaining element 119 may include one or more threaded portions, e.g., on one or more of its proximal or distal ends, which threaded portions correspond to threaded portions within an aperture of the end members, wherein as the retaining element is rotated the corresponding threads cause one or more of the end members 103a and 103b to move axially along the retaining element 119 so as to brought together, thereby causing the implant to expand.

FIGS. 17-25 further illustrate expansible implants according to some embodiments, with additional detail as well as additional features. As described above, an implant of the subject disclosure may include a plurality of opposed plates 6a and 6b. Plates 6a and 6b include a bearing surface 7a and 7b. Bearing surfaces 7a and 7b include a body engaging member, e.g., 8a or 8b, respectively.

As also explained above, the body engaging member may be a bone, tissue, or other body element engaging member dependent upon to what use the implant is designed to be put. In some embodiments, the body engaging member may be a recess, notch, curved support member, or the like and may have a morphology that is complimentary to a bone, tissue, or other body element so as to receive and/or engage the bone, etc. in a snug and/or predetermined manner.

The implant may additionally include end members 3a and 3b and supports 12a, 12b, 13a, 13b, 14a, 14b, 15a, and 15b (and 12c, 13c, 14c, and 15c not shown in FIG. 17), which supports may be configured so as to associate the plates 6a and 6b with the end members 3a and 3b, either directly or indirectly. For instance, the supports may be at least partially positioned under the plates and associated with the plates via an expansion control element 5. For example, one or more of the supports may be associated with one or more of the plates and/or end members via a material web 5, which material web is configured for connecting or otherwise associating a support with a plate and/or an end member and is adapted for being deformed, for instance, elastically or plastically so as to control the expansion of the implant. As illustrated, plates 6a and 6b include wing portions 9a-9d, however, as described above wing portions need not be included. Rather, plates 6a and 6b may be comprised of a central portion 30, which central portion may include recess 8, for engaging a body portion.

The implant may additionally include a retaining element 19, which retaining element may be configured for moveably associating with the end members such that as the retaining element is engaged the plates of the implant move away from a central longitudinal axis thereby expanding the implant. The retaining element as illustrated in the noted figures may include the same features and operation as detailed above.

Figure 17:
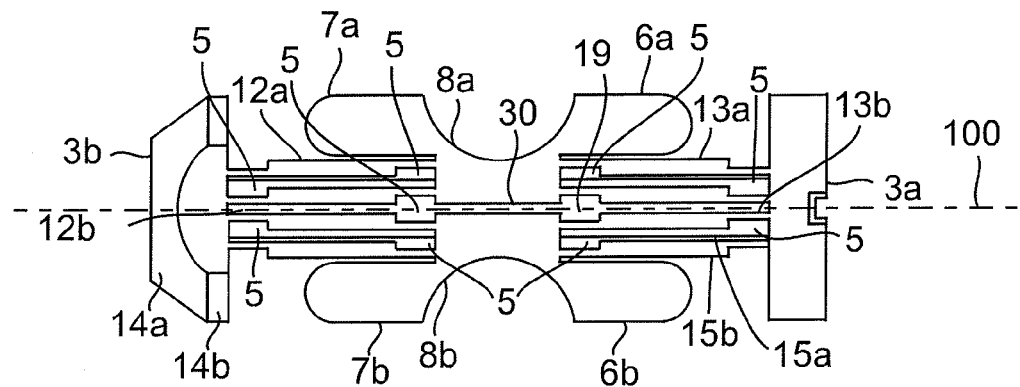
FIG. 17 illustrates a perspective view of an embodiment according to the disclosure of an expansible implant with a recess and a retaining element, in a resting position.
Figure 18:
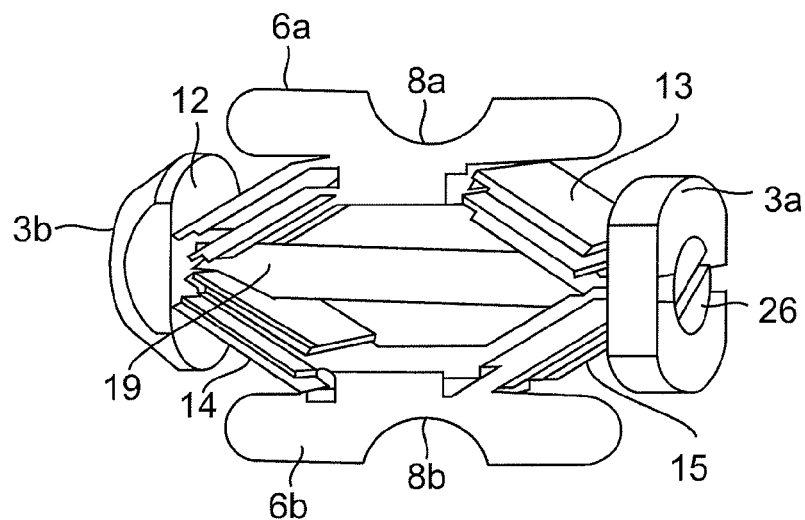
FIG. 18 illustrates the example of FIG. 17, in opened-out position.

As illustrated in FIG. 17, the retaining element may not be engaged when the implant is in a contracted configuration. As illustrated in FIG. 18, the retaining element may be engaged when the implant is in an expanded configuration. The retaining element may be engaged in any suitable manner dependent upon the design of the retaining element and the desired function of the illustrated embodiment (in some embodiments, the implant may be used without the retaining element). For instance, where the retaining element is configured as a screw, the retaining element may be engaged by being rotated. However, where the retaining element is configured as a rivet or wire, the retaining element may be engaged by being pulled and the like. As illustrated, the retaining element 19, according to some embodiments, includes a head portion 26, which head portion may be configured for fitting within a recess of the end member 3a and may include a transverse groove (or other recess, e.g., hex, Phillips, and the like) for receiving an engagement tool, which tool is designed for associating with the retaining element and engaging the retaining element thereby causing the implant to expand. The end member 3a may include a recess for receiving the head member and a notch portion (for example).

At least some of the disclosed implant embodiments, as briefly noted earlier in the application, may be used in methods of using or methods of treatment, for the alleviation of back pain and/or the restoration and/or treatment of adverse spinal conditions. For instance, the implant may be inserted between two vertebrae, for example, to retain or expand a spacing there between.

Figures 19, 20:
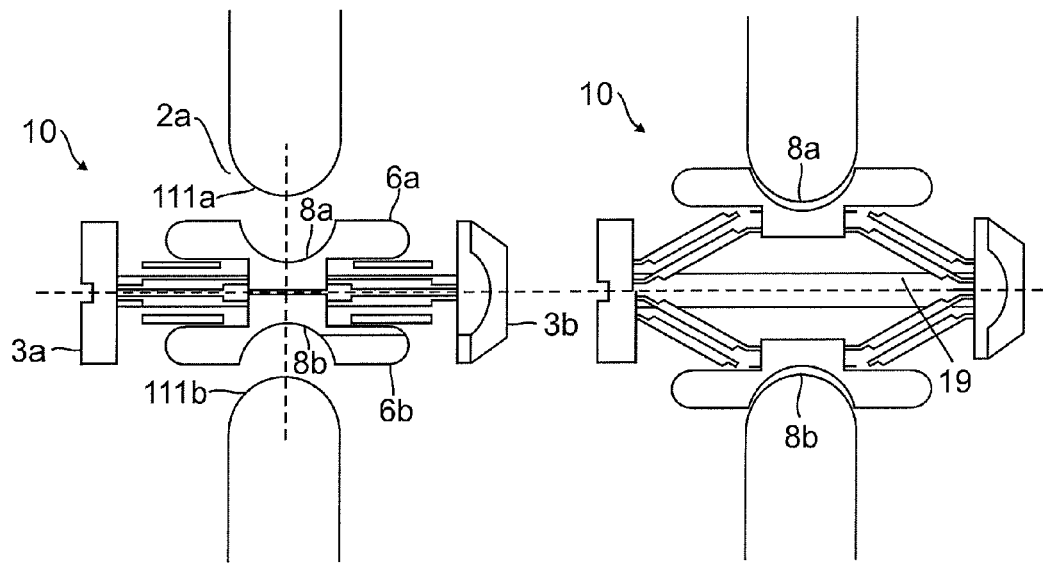
FIG. 19 illustrates a lateral view of the implant of FIG. 17, as it would be post deployment between two surfaces/portions but pre-expansion.
FIG. 20 illustrates a lateral view of the implant of FIG. 17, as it would be post deployment between two surfaces and post-expansion.
Figure 21:
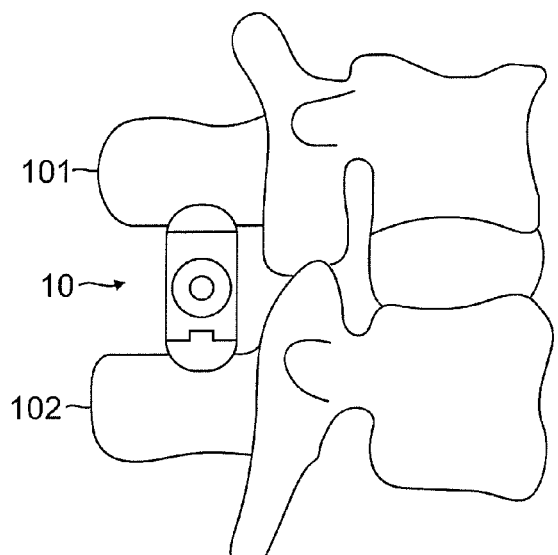
FIG. 21 illustrates a side view of the implant of FIG. 17, as it would be post deployment between two surfaces and post-expansion.

FIGS. 19-21 illustrate an expansible implant of the subject disclosure as it would be employed as an intervertebral implant between two vertebrae where one or more of the vertebrae and/or the space between the vertebrae needs to be retained or restored. Together FIGS. 19-21 illustrate steps of a general method for restoring a portion of a spinal column. For instance, as illustrated in FIG. 19, the method involves the step of inserting (e.g., percutaneously) an expansible implant 10 according to some embodiments, in a collapsed configuration between two vertebrae, e.g., between adjacent spinous processes.

Specifically, in some embodiments, the method includes the implant being inserted and positioned in such a manner that the recesses 8a and 8b of the plates 6a and 6b align with a portion of a vertebrae 111a and 111b in a plane of expansion 2a (for example), such that as the implant 10 is expanded plates 6a and 6b move outwardly from a central axis 100, in the plane of expansion 2a, the recesses 8a and 8b engage the corresponding vertebrae portions 111a and 111b.

As illustrated in FIG. 20, once inserted and positioned between the bone portions, the retaining element 19 of the expansible implant 10 may be engaged and the implant expanded so that the recesses 8a and 8b engage the associated bone portions 111a and 111b, respectively. For instance, in some embodiments, the bone portions 111a and 111b fit snugly into recesses 8a and 8b, for example, where the recesses have been configured to accommodate the morphology of the bone. FIG. 21 illustrates a fully expanded expansible implant once it has been deployed between the two portions of two adjacent bones 101 and 102, for instance, adjacent spinous processes.

Figure 22:
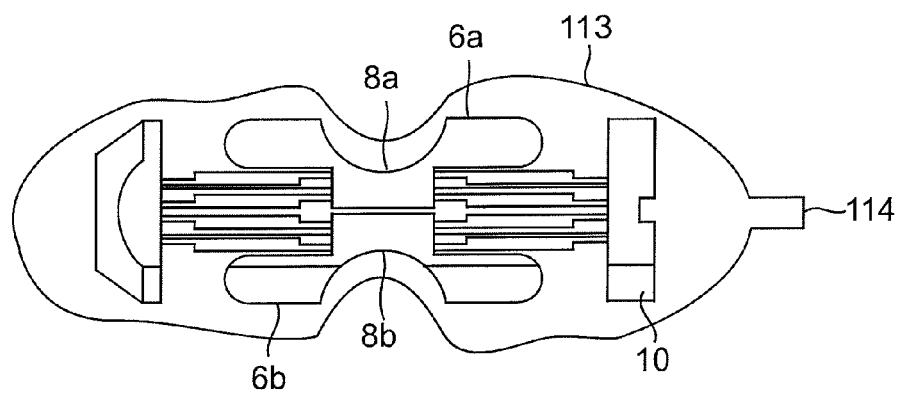
FIG. 22 illustrates a perspective view of one embodiment according to the disclosure of an expansible implant with a recess, a retaining element, and an envelope, in a resting position.
Figure 23:
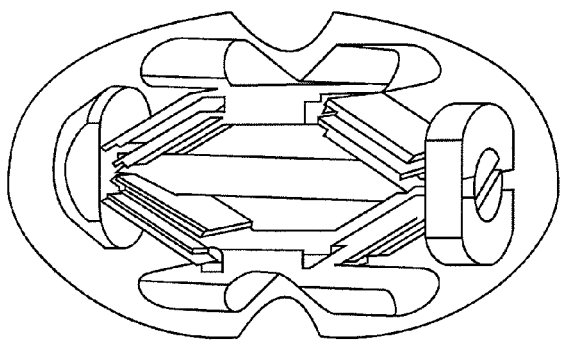
FIG. 23 illustrates the example of FIG. 22, in opened-out position.

FIGS. 22-25 illustrate an expansible implant containing an envelope member as it would be employed as an intervertebral implant between two different vertebral bodies where one or more the vertebrae and/or the space between the bones needs to be restored. FIG. 22 illustrates the implant 10 with the envelope member 113 prior to insertion within a body wherein the implant 10 is in a contracted or collapsed configuration and the envelope member 113 is not expanded (e.g., not inflated). FIG. 23 illustrates the implant 10 with the envelope member 113 as the implant 10 and envelope member 113 would be post insertion in their expanded configurations.

Figure 24:
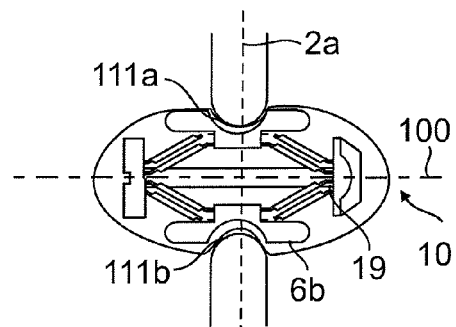
FIG. 24 illustrates a lateral view of the implant of FIG. 22, as it would be post deployment between two surfaces and post-expansion.
Figure 25:
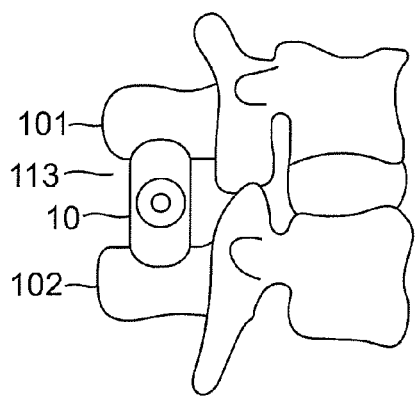
FIG. 25 illustrates a side view of the implant of FIG. 22, as it would be post deployment between two surfaces and post-expansion.

Together FIGS. 24-25 illustrate the steps of a general method for restoring a portion of a spinal column using an implant with an expandable envelope member. For instance, the method involves inserting, e.g., percutaneously, an expansible implant 10 with an envelope member 113 into a body, wherein the envelope member is deflated and the implant is in a collapsed configuration. See FIG. 22. The implant may be inserted, for instance, between two surfaces, e.g., intervertebral bone surfaces, in need of restoration, such as between adjacent spinous processes.

As illustrated in FIG. 24, the implant is inserted and positioned in such a manner that the recesses 8a and 8b of the plates 6a and 6b align with a portion of the bone 111a and 111b in a plane of expansion 2a, such that as the implant 10 is expanded plates 6a and 6b move outwardly from a central axis 100, in the plane 2a, the recesses 8a and 8b engage the bone portions 111a and 111b.

Once inserted and positioned between the two vertebrae, the retaining element 19 of the expansible implant 10 may be engaged and the implant expanded so that the recesses 8a and 8b engage portions 111a and 111b, respectively. Once the implant is expanded, the envelope member 113 may be expanded. Alternatively, the two elements may be expanded simultaneously together. For instance, by the insertion of a fluid, e.g. particulate matter and/or cement, within a lumen of the envelope member, such as through an insertion receiving opening 114 of the envelope member, the envelop member may be filled and expanded either with or without vertebral height restoration. Once the envelope member has been filled, the opening 114 may be sealed, for instance, by any means well known in the art In some embodiments, as illustrated in FIG. 24, the bone portions 111a and 111b fit snugly into recesses 8a and 8b. In this manner, although the envelope 113 is expanded, the expansion of the envelope does not result in a deformation of the recess portion 8 of the plates 3a and 3b. Accordingly, in some embodiments, the recesses 8 and envelope member 113 have been configured to associate with one another in such a manner as to accommodated the morphology of the associated bone portion/surface. FIG. 25 illustrates a fully expanded expansible implant with a fully expanded envelope member once it has been deployed between two portions of two adjacent bones 101 and 102, for instance, adjacent spinous processes.

Figure 26A:
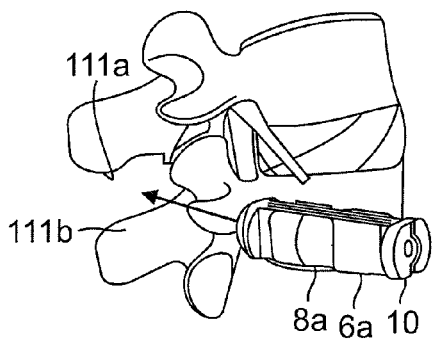
FIG. 26A-D illustrate stages of a method of deploying an expansible implant between two bone surfaces in accordance with some embodiments of the disclosure.
Figure 26B:
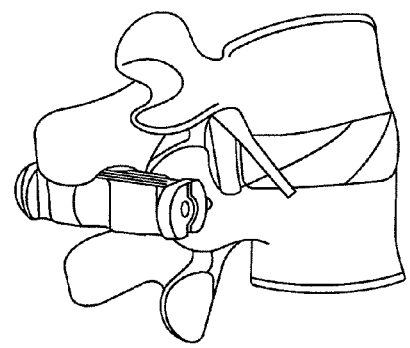
Figure 26C:
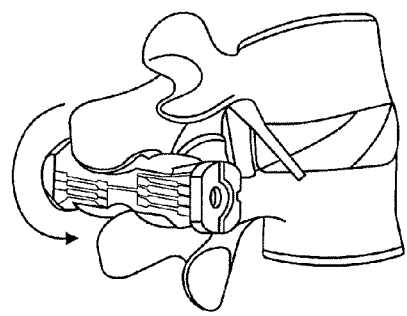
Figure 26D:
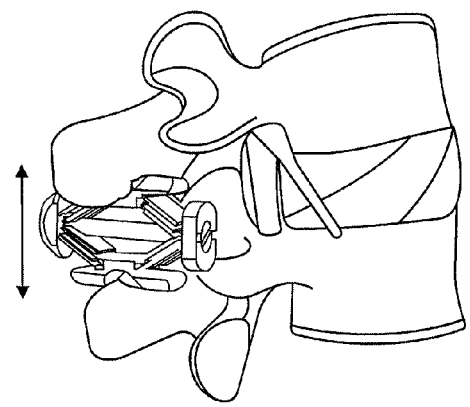

FIG. 26A-D illustrates the deployment of an expansible implant of the subject disclosure as an intervertebral implant between two different vertebral bones wherein one or more the bones themselves and/or the space between the bones needs to be restored. As depicted in FIG. 26A, the method involves the step of inserting (e.g., percutaneously) an expansible implant 10 of the subject disclosure in a collapsed configuration into a body, for instance, between two bones, e.g., bone portions, in need of restoration, such as between adjacent spinous processes 111a and 111b. For example, in a percutaneous approach, a sharp instrument may be inserted between the two spinal processes into the interspinous ligament, performing a hole which will accept the insertion of the implant.

In some embodiments, as illustrated in FIG. 26 B, the method includes the implant 10 being inserted between two opposing bone portions 111a and 111b and positioned in such a manner that the recesses 8a and 8b of the plates 6a and 6b align with the associated bone portions 111a and 111b. For instance, the implant may be inserted in a symmetrical way along the sagital plane.

As illustrated in FIG. 26 C, once inserted and positioned, the implant may be rotated clockwise or counter-clockwise by any amount, e.g., by about 45° to about 135°, for instance, about 90°, so that the implant 10 is in an expansion position. For example, a position wherein the recesses 8a and 8b of the plates 6a and 6b are both aligned and in plane with a portion of the bone portions 111a and 111b along plane 2a, such that as the implant 10 is expanded plates 6a and 6b move outwardly from a central axis 100, in the plane of expansion 2a, the recesses 8a and 8b engage the bone portions 111a and 111b. The implant may be rotated by any suitable means, for instance, via the rotation of an implant holder associated therewith.

For instance, in some embodiments, the implant may be held in place in association with an implant holder, whereby the implant holder may be rotated thereby rotating the implant. For example, the implant holder or the part of the implant holder where the implant is associated may be rotated. In this manner, the implant may easily be inserted through an opening created in a body and rotated into correct orientation so as to be aligned with a suitable plane of expansion without causing substantial stress on the bones, e.g., spinal process. Further, in some embodiments, the rotating allows for the implant to have a good, e.g., tight fit, between the implant, e.g., recess surface, and the bone portion, e.g., spinal process, in contact therewith. In some embodiments, the implant may be larger in one direction than another. Thus, the implant may be inserted with the small height in the direction of the expansion. The higher height may therefore be positioned into the transversal plane. Hence, by rotating the implant the higher height is positioned into the direction of expansion. The recesses may then come into place, for instance, in contact with the spinous bone. In this manner, for example, the implant may be introduced between the spinous processes and placed between the vertebrae prior to expansion, without constraining the spine.

Once rotated so that plates 6a and 6b are aligned in plane 2a between two bone portions, e.g., spinous processes, a retaining element may be inserted through an aperture of end plates 3a and 3b and moveably associated there with such that when the retaining element is engaged the implant is expanded as illustrated in FIG. 26 D. For instance, as shown in FIG. 26 D, once inserted, rotated (if necessary), and positioned between two bones in need of restoration, the retaining element 19 of the expansible implant 10 is engaged and the implant is expanded so that the recesses 8a and 8b engage bone portions 111a and 111b, such that the restoration surfaces 111a and 111b fit snugly into recesses 8a and 8b. Although the retaining element is depicted as being associated with the aperture post implantation of the body 10, it is to be noted that the retaining element may be inserted into the recess prior to implantation of the device, such that the device is essentially pre-assembled prior to implantation. In such an embodiment, the procedure for expansion of the implant may essentially be the same.

It will thus be seen that the disclosure attains the objects made apparent from the preceding description. Since certain changes may be made without departing from the scope of the present disclosure, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current disclosure.

While the disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the disclosure. All such modifications are intended to be within the scope of the claims appended hereto.

What is claimed is:

1. An intervertebral expansible implant, comprising:
a plane of expansion intrinsic to the implant, wherein the implant includes a first length corresponding to a contracted configuration and a second length shorter than the first length corresponding to an expanded configuration;
first and second opposed plates wherein each plate includes a recess configured for engaging a portion of a respective vertebrae of two vertebrae adjacent each respective plate during use of the implant, wherein the first and second plates are intended to move away from one another according to the plane of expansion as the implant is expanded;
at least first and second implant end members monolithically integral with each of the opposed plates, wherein the opposed plates move away from one another as the end members are brought towards one another;
at least a first support and a second support, wherein each support is connected to respective first or second end members, and is disposed between the respective first or second end members and the first or second opposed plates, wherein each support is separated from a winged portion of at least one of the first and second opposed plates by a transverse slot extending over a length of each support; and
a retaining element configured to be retained by the implant after expansion to retain the implant, once expanded, in the expanded configuration, wherein:
the retaining element comprises a shaft integral with a head portion, wherein the head portion is larger than the shaft, the head portion including a top-surface,
the first end member including an end-surface and a head-recess in the end-surface arranged adjacent to at least one aperture provided in the first end member, the at least one aperture configured for receiving one end of the retaining element,
the at least one aperture is sized to receive and pass the shaft of the retaining element, and
the head-recess is sized to receive and retain the head portion of the retaining element, such that when the head portion of the retaining element is fully received into the head-recess, a top surface of the head portion sits flush with or below the end-surface.

2. The expansible implant according to claim 1, wherein the first end member is located at a proximal end of the implant, and the second member is located at a distal end of the implant;
a first aperture is provided in the second end member positioned distally on the implant;
the at least one aperture is a second aperture provided in the first end member;
the retaining element includes at least an abutment provided on a proximal end of the retaining element;
the first aperture is configured for receiving a distal portion of the retaining element, at least the distal end of the retaining element includes a mating area corresponding to a mating area of the first aperture;
the second aperture is configured for receiving a proximal portion of the retaining element such that when the mating area of the distal end of the retaining element mates with the mating area of the first aperture, the abutment is positioned proximate an exterior side of the proximal end member of the implant, thereby enabling the retaining element to retain the implant in the expanded configuration.

3. The expansible implant according to claim 2, wherein the mating areas comprise corresponding screw threads.

4. The expansible implant according to claim 3, wherein the mating areas comprise corresponding screw threads, and wherein upon the abutment abutting with the head-recess, further threading of the screw threads corresponds to expansion of the implant.

5. The expansible implant according to claim 4, wherein the degree of expansion of the implant is controlled by the amount of threaded engagement of the corresponding screw threads.

6. The expansible implant according to claim 3, wherein the second aperture comprises screw threads and in place of or in addition to the abutment, the proximal end of the retaining element includes screw threads corresponding to the screw threads of the second aperture, and upon the corresponding screw threads of the second aperture and proximal end of the retaining element being engaged with one another, the retaining element retains the implant in the expanded configuration.

7. The expansible implant of claim 1, further comprising an expandable envelope member.

8. The expansible implant of claim 7, further comprising a material configured to aid in retaining the expanded configuration of the implant.

9. The expansible implant of claim 8, wherein the material comprises a bone cement.

10. The expansible implant of claim 7, wherein the expandable envelope member at least partially covers the implant.

11. The expansible implant according to claim 1, wherein the retaining element is selected from the group consisting of: a screw, a rivet, a wire and combinations thereof.

12. The expansible implant according to claim 1, wherein a length of the retaining element corresponds to the first length of the implant.

13. A method for restoring an intervertebral space between two vertebral bones, comprising the steps of:
    percutaneously inserting into a body an expansible implant, wherein the expansible implant includes a contracted and an expanded configuration, and wherein the implant includes a first length corresponding to contracted configuration and a second length shorter than the first length corresponding to the expanded configuration, the implant comprises:
        first and second opposed plates, wherein each plate includes a recess configured for engaging a respective portion of the two vertebral bones during use of the implant, wherein the first and second plates are intended to move away from one another toward the respective vertebral bones as the implant is expanded;
        first and second implant end members monolithically integral with each of the opposed plates, wherein the opposed plates move away from one another as the end members are brought towards one another;
        at least a first support and a second support, wherein each support is connected to respective first or second end members, and is disposed between the respective first or second end members and the first or second opposed plates, wherein each support is separated from a winged portion of at least one of the first and second opposed plates by a transverse slot extending over a length of each support; and
    a retaining element configured to be retained by the implant after expansion to retain the implant, once expanded, in the expanded configuration, wherein:
        the retaining element comprises a shaft integral with a head portion, wherein the head portion is larger than the shaft, the head portion including a top-surface;
        at least one aperture provided in the first end member, the at least one aperture configured for receiving one end of the retaining element;
        the first end member including an end-surface and a head-recess in the end-surface arranged adjacent the aperture,
        wherein the aperture is sized to receive and pass the shaft of the retaining element, and
        the head-recess is sized to receive and retain the head portion of the retaining element, such that a top surface of the head portion sits flush with or below the end-surface;
    positioning the implant between the vertebral bones; and
    expanding the implant from the contracted configuration to the expanded configuration thereby restoring the intervertebral space. expanded, the retaining element retains the implant in the expanded configuration.

14. The method according to claim 13, wherein the positioning comprises aligning the recesses with respective vertebral bones such that when the implant is expanded the recesses engage a portion of the vertebral bones.

15. The method according to claim 14, wherein the positioning further includes rotating the implant so as to align the recesses with the vertebral bones.

16. The method according to claim 15, wherein the expansion or rotation of the implant causes the recesses to contact and engage a portion of the vertebral bones.

17. The method according to claim 16, wherein the portion of the vertebral bones fit within the recess of the implant.

18. The method according to claim 13, wherein the implant further comprises an envelope member.

19. The method according to claim 18, vherein the envelope member is expanded prior to or after expansion of the implant.

20. The method according to claim 19, wherein the envelope member is expanded via the expansion of the implant.

21. The method according to claim 18, wherein the envelope member is expanded by the addition of a fill material therein.

22. The method according to claim 13, wherein the implant is expanded to the expanded configuration by engagement of the retaining element.

23. The method according to claim 13, wherein once the implant is expanded, the retaining element retains the implant in the expanded configuration.

24. The method according to claim 13, wherein the implant is inserted in a collapsed configuration.

* * * * *